(12) United States Patent
Wang et al.

(10) Patent No.: US 9,593,072 B2
(45) Date of Patent: Mar. 14, 2017

(54) PROCESS FOR PREPARING N-ACYL AMINO ACID SALTS

(71) Applicant: STEPAN COMPANY, Northfield, IL (US)

(72) Inventors: Bing Wang, Mount Pleasant, SC (US); Gregory P. Dado, Chicago, IL (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 15/017,465

(22) Filed: Feb. 5, 2016

(65) Prior Publication Data

US 2016/0152555 A1    Jun. 2, 2016

Related U.S. Application Data

(63) Continuation of application No. PCT/US2014/050219, filed on Aug. 7, 2014.

(60) Provisional application No. 61/867,500, filed on Aug. 19, 2013.

(51) Int. Cl.
| | | |
|---|---|---|
| *C07C 231/02* | (2006.01) | |
| *C07D 233/64* | (2006.01) | |
| *C07D 207/16* | (2006.01) | |
| *C07C 233/47* | (2006.01) | |

(52) U.S. Cl.
CPC .......... *C07C 231/02* (2013.01); *C07C 233/47* (2013.01); *C07D 207/16* (2013.01); *C07D 233/64* (2013.01)

(58) Field of Classification Search
CPC .................................................. C07C 231/02
See application file for complete search history.

(56) References Cited

U.S. PATENT DOCUMENTS

| | | |
|---|---|---|
| 3,836,551 A | 9/1974 | Schroeder et al. |
| 4,380,646 A | 4/1983 | Franzmann |
| 5,856,538 A | 1/1999 | Strecker et al. |
| 5,898,084 A | 4/1999 | Oftring et al. |
| 6,703,517 B2 | 3/2004 | Hattori et al. |
| 6,828,452 B2 | 12/2004 | Raths et al. |
| 8,093,414 B2 | 1/2012 | Klug et al. |
| 9,156,777 B2 | 10/2015 | Wang et al. |
| 2004/0063980 A1 | 4/2004 | Raths et al. |
| 2006/0239952 A1 | 10/2006 | Hattori |
| 2009/0062177 A1 | 3/2009 | Tsaur |
| 2009/0156450 A1 | 6/2009 | Tsaur |
| 2010/0075881 A1 | 3/2010 | Tsaur |
| 2010/0273879 A1 | 10/2010 | Klug et al. |
| 2010/0305358 A1 | 12/2010 | Klug et al. |
| 2011/0245125 A1 | 10/2011 | Tsaur et al. |
| 2013/0029899 A1 | 1/2013 | Hermanson et al. |
| 2013/0030197 A1 | 1/2013 | Harichian et al. |
| 2013/0030198 A1 | 1/2013 | Harichian et al. |
| 2013/0030199 A1 | 1/2013 | Harichian et al. |
| 2013/0030200 A1 | 1/2013 | Harichian et al. |
| 2013/0030201 A1 | 1/2013 | Harichian et al. |
| 2013/0030202 A1 | 1/2013 | Harichian et al. |
| 2013/0030203 A1 | 1/2013 | Harichian et al. |

FOREIGN PATENT DOCUMENTS

| | | |
|---|---|---|
| DE | 4408957 | 9/1995 |
| DE | 19525512 A1 | 1/1997 |
| EP | 1672055 | 6/2006 |
| WO | 9507881 | 3/1995 |
| WO | 2013014268 | 1/2013 |
| WO | 2014008103 A2 | 1/2014 |

OTHER PUBLICATIONS

E Jungermann et al., J. Am. Chem. Soc. 78 (1956) 172.
K. Kochetkov et al., Bull. Acad. Sci. USSR 39 (1990) 2311.
PCT Search Report mailed in PCT/US2013/048341 on Oct. 2, 2013.
PCT Search Report mailed in PCT/US2014/050219 on Nov. 17, 2014.
PCT International Preliminary Report on Patentability dated Feb. 23, 2016 from corresponding Applicaiton No. PCT/US2014/050219, 7 pages.

*Primary Examiner* — Yate K Cutliff
(74) *Attorney, Agent, or Firm* — Dilworth IP, LLC

(57) ABSTRACT

N-Acyl amino acid salt compositions and an improved process for making them from fatty alkyl esters are disclosed. The process comprises reacting a fatty alkyl ester with an amino acid salt in the presence of an alkoxide catalyst at a pressure of at least 5 psig. At least 10 mole percent of catalyst is used based on the amount of fatty alkyl ester used as a reactant. Pressure and a minimum level of alkoxide catalyst are needed to give high fatty alkyl ester conversions and good yields of the desired N-acyl amino acid salt. The resulting N-acyl amino acid salt compositions have low color, an acceptable level of fatty acid soaps, and a small proportion of di-acylated by-products. Single-phase mixtures produced by combining various amino acid salts with glycinates, or by using an excess of either the fatty alkyl ester or amino acid salt, promote high conversions when the mixtures are reacted to give the desired N-acyl amino acid salt.

15 Claims, No Drawings

PROCESS FOR PREPARING N-ACYL AMINO ACID SALTS

This application is a continuation under 35 U.S.C. §365 of PCT/US2014/050219, filed Aug. 7, 2014, which claims the benefit of U.S. provisional application 61/867,500, filed Aug. 19, 2013.

FIELD OF THE INVENTION

The invention relates to N-acyl amino acid salts and processes for preparing them.

BACKGROUND OF THE INVENTION

N-Acyl amino acid salts are anionic surfactants useful in laundry detergents, household or industrial cleaners, foamers, emulsifiers, personal cleansers, and other applications. Because they are often exceptionally mild, the salts are particularly valuable for personal care formulations.

In general, N-acyl amino acid salts have been underutilized, due at least in part to challenges in manufacturing them. N-Acyl amino acid salts can be made from the corresponding fatty acyl chlorides and amino acid salts using Schotten-Baumann chemistry (see, e.g., *J. Am. Chem. Soc.* 78 (1956) 172 and U.S. Pat. No. 6,703,517), but this process is expensive and generates an equimolar amount of undesirable salt by-product. In an alternative synthetic method, a fatty acid is reacted with an amino alcohol to give a fatty amide, which is then oxidized to give the N-acyl amino acid (see, e.g., U.S. Pat. No. 8,093,414). This process is hampered by relatively low yields, low selectivities in the oxidation step, the use of precious metal catalysts, and the need for a conventional organic workup.

In other known processes, the N-acyl amino acid salt is made from a fatty acid. For example, EP 1672055 and U.S. Pat. Appl. Publ. No. 2006/0239952 describe the synthesis of N-acyl glycinates by reacting a fatty acid with glycine. This process generates a relatively high proportion of di- and tripeptide by-products (di- and triglycinates), which may or may not be desirable depending upon the intended use; conversion to the mono-acylated product is about 92%. U.S. Pat. No. 3,836,551 teaches to react fatty acids with amino acid salts either in the molten fluid phase (i.e., without a solvent), in solution using a polar aprotic solvent (such as dimethyl sulfoxide or N,N-dimethylformamide), or in suspension with a nonpolar organic solvent (e.g., xylene). Typical reaction times are about 9 hours, and by-products are not discussed. Generally, the fatty acid route is also less preferred because it requires a high reaction temperature, which leads to undesirable color development in the N-acyl amino acid salt.

U.S. Pat. No. 5,898,084 describes the preparation of N-acyl amino acid salts by reacting a mono-, di-, or triglyceride with an amino acid salt in the presence of a strong base. In the examples, colza oil (a triglyceride) is reacted with sodium sarcosinate in the presence of sodium methoxide/methanol, and the reaction continues until glycerides are no longer detected. A typical organic workup follows. The reference indicates that the glycerin produced in the course of the reaction either remains in the reaction mixture or is partly or wholly removed in the conventional workup. At the conclusion of the reaction, the mixture is typically a viscous paste.

Fatty alkyl esters have also been used as starting materials. U.S. Pat. No. 5,856,538 teaches to react a fatty alkyl ester (e.g., methyl oleate) with an amino acid salt and a 30-150% molar excess of a strong base, e.g., sodium methoxide/methanol solution (see col. 2, l. 65 to col. 3, l. 2 and Examples 2 and 3). Sodium sarcosinate is used in the examples, although other amino acid salts are taught as suitable. The '538 patent teaches (col. 3, ll. 22-27) that the reaction is normally carried out "under atmospheric pressure; although autogenous pressure or elevated pressure is possible, it has no further advantages." WO 95/07881 teaches a method of preparing N-acyl sarcosinates starting from fatty esters. The reference indicates that alcohol solvents (e.g., 1-propanol, 1-butanol, isobutyl alcohol, propylene glycol, ethylene glycol) can be used to reduce viscosity during the amidation reaction. In the examples, the solvent is used to remove water by azeotropic distillation.

Recent Unilever publications describe the preparation of fatty N-acyl amido surfactants from fatty alkyl esters and amino acid salts in a low-molecular-weight polyol such as glycerol or propylene glycol as a reaction medium (see U.S. Pat. Appl. Publ. Nos. 2013/0029899, 2013/0030197, 2013/0030198, 2013/0030199, 2013/0030200, 2013/0030201, 2013/0030202, and 2013/0030203). Comparative runs using water, alcohols, or toluene instead of glycerol provided very low yields. Catalysts taught for the process include "alkaline and alkaline earth metal containing hydroxides, phosphates, sulphates and oxides including calcium oxide, magnesium oxide, barium oxide, sodium oxide, potassium oxide, calcium hydroxide, magnesium phosphate and mixtures thereof" (see the '203 publication at paragraph [0031]). Calcium oxide is used in the examples.

The preparation of N-acyl amino acid salts is particularly challenging when the reactants are fatty alkyl esters (particularly fatty methyl esters) and alkali metal glycinates, as in the preparation of sodium cocoyl glycinate, sodium myristyl glycinate, or sodium lauryl glycinate. This reaction is troublesome due to a lack of reagent compatibility, solidification of the reaction mixture at elevated process temperatures, color development, severe foaming during methanol removal, and significant by-product generation. Too often, conditions cannot be found that provide low-color N-acyl amino acid salts in high yield with minimal generation of fatty acid soaps and dipeptide by-products.

In sum, an improved process for making N-acyl amino acid salts is needed. In particular, the industry needs a process that avoids salt generation and the selectivity issues of other known routes. Preferably, the particular difficulties that complicate the preparation of N-acyl glycinates from fatty alkyl esters could be overcome. An ideal process would give high yields of low-color N-acyl amino acid salts with a reduced proportion of fatty acid soaps and dipeptide by-products.

SUMMARY OF THE INVENTION

In one aspect, the invention relates to N-acyl amino acid salt compositions and an improved process for making them from fatty alkyl esters. The process comprises reacting a fatty alkyl ester with an amino acid salt in the presence of an alkoxide catalyst. The reaction is performed at a pressure of at least 5 psig. At least 10 mole percent of catalyst is used based on the amount of fatty alkyl ester used as a reactant. We surprisingly found that pressure and a minimum level of an alkoxide catalyst are needed to give high fatty alkyl ester conversions and good yields of the desired N-acyl amino acid salt. The resulting N-acyl amino acid salt compositions, which can be formulated at high actives levels, have low color, an acceptable level of fatty acid soaps, and a small proportion of di-acylated by-products.

In another aspect, the invention relates to an improved way to isolate an N-acyl amino acid salt. In this process, the N-acyl amino acid salt is isolated from unreacted starting materials (fatty alkyl ester, amino acid salt) in the N-acyl amino acid salt composition by forming a slurry of the composition in a $C_1$-$C_4$ alcohol, recovering the N-acyl amino acid salt from the slurry, and drying the N-acyl amino acid salt.

In another aspect, the invention relates to a single-phase mixture comprising a fatty alkyl ester and an amino acid salt. The single-phase mixture may comprise at least 10 mole %, based on the amount of fatty alkyl ester, of an alkoxide catalyst. In another aspect, the single-phase mixture comprises an amino acid salt mixture; this salt mixture comprises a non-glycinate amino acid salt and at least 20 mole % of a glycinate salt. In another aspect, the single-phase mixture comprises at least a 30 mole % excess of the fatty alkyl ester or at least a 30 mole % excess of the amino acid salt. We surprisingly found that achieving a single-phase mixture of starting materials by one of the above methods is valuable for achieving good conversions when reacting amino acid salts with fatty alkyl esters to give the corresponding N-acyl amino acid salts.

DETAILED DESCRIPTION OF THE INVENTION

In one inventive process, a fatty alkyl ester reacts with an amino acid salt in the presence of sufficient alkoxide catalyst under pressure to give an N-acyl amino acid salt composition.

Suitable fatty alkyl esters are lower alkyl esters of linear or branched, saturated or unsaturated fatty acids. The fatty alkyl ester can be made, for example, by esterifying a fatty acid with an alkanol or by transesterifying a triglyceride, which is typically an animal or vegetable fat or oil, with an alkanol. Consequently, the fatty portion of the ester will typically have 6-22 carbons with a mixture of saturated and internally unsaturated chains.

In a preferred aspect, the fatty alkyl ester is a lower alkyl ester obtained by fractionation. Thus, saponification of a fat or oil provides a fatty acid, which can be reacted with a lower alkanol to give a mixture of esters, typically methyl esters. Fractionation of this mixture provides fatty alkyl esters having a desired average carbon number range. Alternatively, the fat or oil is transesterified with an alkanol to give the esters in one step prior to fractionation.

Depending on the source, the fatty ester may have a preponderance of $C_{16}$-$C_{22}$ component. For instance, methanolysis of soybean oil provides the saturated methyl esters of palmitic ($C_{16}$) and stearic ($C_{18}$) acids and the unsaturated methyl esters of oleic ($C_{18}$ mono-unsaturated), linoleic ($C_{18}$ di-unsaturated), and α-linolenic ($C_{18}$ tri-unsaturated) acids. Preferred fatty alkyl esters derive from $C_6$-$C_{22}$ fatty acids or their mixtures, preferably $C_8$-$C_{18}$ fatty acids or their mixtures. In some instances, $C_{12}$-$C_{14}$ fatty acids may be preferred. Examples include methyl caprate, methyl myristate, methyl laurate, and methyl esters from coconut oil. Preferred fatty alkyl esters derive from $C_1$-$C_4$ alkanols, preferably methyl or ethyl esters, most preferably methyl esters.

Suitable amino acid salts are alkali metal and alkaline earth metal salts of amino acids. The amino acid can be, for example, alanine, valine, leucine, isoleucine, phenylalanine, tryptophan, methionine, aspartic acid, glutamic acid, glycine, sarcosine, serine, threonine, cysteine, tyrosine, glutamine, lysine, arginine, and histidine. Preferred amino acids have a primary amino group. Preferred are alkali metal salts, particularly sodium and potassium salts, of amino acids selected from glycine, alanine, glutamine, glutamic acid, and aspartic acid. Glycinates are particularly preferred. Examples 1-18 below illustrate the preparation of N-acyl amino acid salts from glycine, alanine, and glutamine.

The molar ratio of amino acid salt to fatty alkyl ester can vary over a wide range, and the ratio preferred for use will depend on the identity of the amino acid salt, the identity of the fatty alkyl ester, the ability to form a single-phase mixture of starting materials with the selected molar ratio, and other factors. For instance when a glycinate is used as the amino acid salt, it may be acceptable and even preferred to use about equimolar amounts of the reactants, whereas with other combinations of amino acid salts and fatty alkyl esters, it may be more desirable to use an excess of the fatty methyl ester or an excess of the amino acid salt. Thus, when a glycinate is used as the amino acid salt, a molar ratio of amino acid salt to fatty alkyl ester in the range of 0.9:1 to 1.1:1 may be preferred. When a glycinate is not used, an excess of the amino acid salt may be more desirable, for instance, a molar ratio of amino acid salt to fatty alkyl ester in the range of 3:1 to 1.3:1, preferably 2:1 to 1.5 to 1. In other aspects, an excess of the fatty alkyl ester is preferred, for instance, a molar ratio of fatty alkyl ester to amino acid salt in the range of 3:1 to 1.3:1, preferably 2:1 to 1.5:1. Surprisingly, we found that for non-glycinate amino acid salts, when an excess of one of the reactants is used, it may be easier to generate a single-phase mixture of starting materials, and this may lead to better conversion (see Table 3, below).

The reaction of the fatty alkyl ester and amino acid salt is performed in the presence of an alkoxide catalyst. Alkali metal alkoxides such as sodium methoxide, potassium methoxide, sodium ethoxide, and the like, are preferred. We surprisingly found that other alkaline catalysts, including alkali metal hydroxides, alkali metal carbonates, and alkaline earth metal oxides, are much less effective in achieving a desirably high conversion of fatty alkyl ester and a desirably high yield of N-acyl amino acid salt.

The amount of alkoxide catalyst used also matters. Unexpectedly, we found that fatty alkyl ester conversions and N-acyl amino acid salt yields are unacceptable when the alkoxide catalyst is used in an amount less than 10 mole percent based on the amount of fatty alkyl ester. Thus, in the inventive process, at least 10 mole percent, based on the amount of fatty alkyl ester, of the alkoxide catalyst is used. A preferred amount of alkoxide catalyst is 12 to 50 mole percent, more preferably 12 to 30 mole percent, based on the amount of fatty alkyl ester. As shown in the examples below, when less than 10 mole percent of the alkoxide catalyst is used, yields of the N-acyl amino acid salt are typically 30% or less (see Table 2, Comparative Examples 19-25).

Alkoxide catalysts are commercially available in solid form or as solutions in the alcohol from which the alkoxide derives, such as sodium methoxide/methanol, potassium ethoxide/ethanol, or potassium t-butoxide/t-butyl alcohol. The alkoxide is preferably a $C_1$-$C_6$ alkoxide, more preferably a $C_1$-$C_4$ alkoxide, and most preferably a $C_1$ or $C_2$ alkoxide. The alcohol is typically a $C_1$-$C_{10}$ alcohol, preferably a $C_1$-$C_6$ alcohol, more preferably a $C_1$-$C_4$ alcohol, and it need not be the same alcohol from which the alkoxide derives, although this is preferred. Sodium methoxide/methanol, potassium methoxide/methanol, sodium ethoxide/ethanol, and potassium ethoxide/ethanol are most preferred. Examples 6 and 13-15 below illustrate the use of alcohols other than methanol.

In some aspects, the process may be performed in the presence of an added organic solvent (e.g., alcohols, ethers, esters, hydrocarbons, halides, amides, or the like). Preferred organic solvents are alcohols, especially the alcohol from which the alkoxide catalyst derives (e.g., methanol when the catalyst is sodium methoxide). Thus, it may be desirable to add an alcohol to supplement the alcohol that is supplied with the catalyst and/or is generated from reaction of the amino acid salt with the fatty alkyl ester. The added alcohol may be the same as or different from the alcohol from which the catalyst derives or the alcohol liberated from the fatty alkyl ester. Preferably, the added alcohol is the same as that present in the catalyst and is also the same as the alcohol liberated from the fatty alkyl ester. Thus, in one preferred aspect, the catalyst is sodium methoxide or sodium methoxide/methanol, the fatty alkyl ester is a fatty methyl ester, and the added solvent is methanol. The amount of added organic solvent is generally not critical and will depend on many factors. Preferably, the amount of organic solvent used will be within the range of 1 to 200 wt. %, more preferably 15 to 100 wt. %, even more preferably 40 to 80 wt. %, and most preferably 50 to 70 wt. %, based on the amount of fatty alkyl ester.

The reaction of the fatty alkyl ester and the amino acid salt is performed at a pressure of at least 5 psig (i.e., 5 psi above the ambient atmospheric pressure). Preferably, the pressure is within the range of 5 to 50 psig, more preferably from 5 to 30 psig. We surprisingly found that when an alkoxide base is used, even a little added pressure is valuable for converting the fatty alkyl ester to the desired N-acyl amino acid salt. Compare, for instance, the results with 22 mole percent sodium methoxide catalyst at atmospheric pressure (0 psig) in refluxing methanol at 65° C. (Table 2, Comparative Examples 28 and 29) or refluxing methanol/isopropanol at 75° C. (Table 2, Comparative Example 30) versus the results at low pressure (7 psig) in methanol at 66° C. (Table 1, Example 12). In the reactions performed at atmospheric pressure, the yield of amino acid salt is essentially zero. On the other hand, with the same level of catalyst at low pressure, the amino acid salt is obtained in 78% yield.

Pressure alone is not the answer, however. When other basic catalysts are used (e.g., NaOH, $K_2CO_3$, CaO) under 30-35 psig, yields are low or nonexistent (see Table 2, Comparative Examples 27, 31, and 32).

The reaction can be performed at any convenient temperature. Preferably, the reaction is performed at a temperature within the range of 65° C. to 200° C., more preferably from 65° C. to 130° C., most preferably from 65° C. to 100° C.

In a preferred aspect, the process is performed using a combination of relatively low temperature and pressure, in particular, at a temperature from 65° C. to 100° C., more preferably 75° C. to 95° C., and at a pressure within the range of 5 psig to 30 psig, more preferably 10 psig to 25 psig. Under these relatively mild conditions, we found that it is possible to make low-color N-acyl amino acid salts, preferably N-acyl glycinates, in high yield (93+%) while avoiding formation of di-acylated by-products (N-acyl dipeptides) and while minimizing the level of fatty acid soap formed (see Table 1, Examples 16-18).

A polyol may be used if desired, although none is necessary. In some cases, a polyol may be included in an amount effective to keep the reaction mixture fluid. When used, the polyol is preferably glycerin, propylene glycol, or a mixture thereof. "Fluid" means that the reaction mixture maintains good flow properties at the reaction temperature; it remains stirrable and pumpable at reasonable energy demand. The amount of any polyol used will depend on the fatty ester chain length, the nature of the amino acid salt and polyol, the reaction temperature, and other factors. When a polyol is included, it is preferred to use at least 3 wt. %, more preferably at least 10 wt. %, based on the combined amounts of polyol, fatty alkyl ester, and amino acid salt. Examples 2-5 and 7 below (Table 1) illustrate the use of glycerin as a polyol in the inventive process.

Preferably, the reaction mixture will have a final viscosity less than 10,000 cP, more preferably less than 1000 cP, and most preferably less than 200 cP, where each viscosity is measured at the amidation reaction temperature.

Conversion of the amino acid salt to the N-acyl amino acid salt is carried out to any desired degree. For some end-use applications, it may be desirable to convert only a portion of the amino acid salt, thereby giving a mixture of the fatty alkyl ester and the amidation product. Preferably, however, at least 85 mole % of the amino acid salt is converted to the N-acyl amino acid salt. More preferably, at least 90 mole % of the amino acid salt is converted to the N-acyl amino acid salt.

The inventive process makes it possible to minimize the proportion of di- and triacylated by-products (also referred to herein as "di- and tripeptides" or "N-acyl dipeptides" and "N-acyl tripeptides") generated. Preferably, the amount of diacylated by-products is less than 10 mole %, more preferably less than 5 mole %, based on the combined amounts of N-acyl amino acid salt and by-products.

The reaction of the fatty alkyl ester and amino acid salt takes place under conditions basic enough to cause a competing hydrolysis reaction when some water is present. Thus, some of the fatty alkyl ester is normally hydrolyzed to give a fatty acid salt ("soap"). Preferably, water is substantially excluded from the amidation reaction, but a minor proportion of water is acceptable, especially when the reaction conditions are sufficiently mild. Depending on the supplier, the amino acid salts are provided with varying water contents, sometimes up to 5 wt. % or more. As shown in Table 1, we found that the amount of soap generated can be minimized when the reaction conditions are sufficiently mild, for instance, at temperatures within the range of 65° C. to 100° C. and at pressures from 5 psig to 30 psig. Preferably, the N-acyl amino acid salt is generated with less than 20 mole percent, preferably less than 10 mole percent, even more preferably 5 mole percent or less of the corresponding fatty acid soap. As shown in the comparative examples (Table 2), it can be difficult to achieve low fatty acid soap levels.

The desired product is an N-acyl amino acid salt. The salts have broad utility as anionic surfactants and are useful in such industries as personal care, laundry detergents, fabric treatment, industrial or household cleaners, emulsion polymerization, bleaching, and oilfield chemicals, among others. The N-acyl glycinates and N-acyl sarcosinates, particularly the alkali metal salts, are of particular interest in personal care applications such as body washes, shampoos, bar soaps, liquid hand soaps, and the like. The use of glycerin or propylene glycol as a fluidizing agent for the inventive process may be beneficial, particularly for personal care products normally formulated to include glycerin or propylene glycol. Consequently, there may be no need to remove any glycerin or propylene glycol used to prepare the N-acyl amino acid salt.

The preparation of N-acyl amino acid salts can be challenging when the reactants are fatty methyl esters and alkali metal glycinates. This reaction is troublesome due to a lack of reagent compatibility, solidification of the reaction mixture at elevated process temperatures, color development, severe foaming during methanol removal, and significant by-product generation. The unavailability, until now, of a highly economical process has likely hindered broad utilization of N-acyl glycinates, which are exceptionally mild anionic surfactants, in personal care and other applications.

N-Acyl amino acid salts made by the inventive process have low color. Preferably, the salts have an APHA color, measured according to ASTM D1209 using a 20 wt. % aqueous solution in a 40-mm cell, less than 100, preferably less than 50. Low color is desirable, especially for most personal care applications, although it is not necessarily easy to achieve. When calcium oxide is used as the catalyst, for instance, APHA color tends to be much higher (see Table 2, Comparative Example 26).

Aqueous mixtures comprising the N-acyl amino acid salts can be formulated at high actives levels. While it can be challenging to formulate aqueous surfactant compositions at high actives levels, we found that aqueous compositions comprising the inventive N-acyl amino acid salts demonstrate good compatibility at actives contents of at least 20 wt. %, preferably at least 35 wt. %, and up to 50 wt. %. Generally, the highest actives levels are available when a polyol solvent is not included.

In summary, when pressure and enough of an alkoxide base are included, N-acyl amino acid salt compositions having low color, low fatty acid soap content, and a reduced proportion of di-acylated by-products can be generated under mild conditions in high yields with good conversions.

In another aspect, the invention relates to an improved way to isolate an N-acyl amino acid salt. In this process, the N-acyl amino acid salt is isolated from unreacted starting materials (fatty alkyl ester, amino acid salt) in the N-acyl amino acid salt composition by forming a slurry of the composition in a $C_1$-$C_4$ alcohol, recovering the N-acyl amino acid salt from the slurry, and drying the N-acyl amino acid salt. Suitable $C_1$-$C_4$ alcohols are well known and include, for example, methanol, ethanol, 1-propanol, isopropanol, 1-butanol, 2-butanol, isobutanol, tert-butanol, and the like, and mixtures thereof. Methanol and ethanol are preferred. Methanol is particularly preferred. Generally, enough of the $C_1$-$C_4$ alcohol is used to form a slurry of the N-acyl amino acid salt (and unreacted starting materials) in the alcohol. Preferably, the weight ratio of alcohol to amino acid salt is within the range of 2:1 to 100:1, more preferably within the range of 3:1 to 10:1. The N-acyl amino acid salt can be recovered from the slurry by any suitable means, including decantation, filtration, centrifugation, or the like. It is convenient to filter the slurry through fritted glass or the like, followed by washing of the N-acyl amino acid salt with additional $C_1$-$C_4$ alcohol. The salt is then dried at or above ambient temperature by any desired method to remove any remaining alcohol.

In another aspect, the invention relates to a single-phase mixture comprising a fatty alkyl ester, an amino acid salt, and at least 10 mole %, based on the amount of fatty alkyl ester, of an alkoxide catalyst. As used herein, "single-phase mixture" refers to a mixture of the starting materials for making the N-acyl amino acid salt. By "single-phase," we mean that the mixture of starting materials is a homogeneous liquid or a suspension that is free of a separated fatty alkyl ester phase. We surprisingly found that when the starting materials are combined and mixed briefly under ambient conditions, and a single-phase liquid mixture of the reactants results, subsequent reaction of the starting materials is generally successful in achieving high conversions of the amino acid salts to the corresponding N-acyl amino acid salts. It should be noted that while the reaction is in progress, one or more phases may be present in the reaction mixture. However, before the reaction has taken place to any significant degree, the mixture of starting materials will be a single-phase mixture; i.e., substantial phase separation of the fatty alkyl ester liquid will not be evident. In contrast, when the starting materials to be used (including the alcohol solvent) are combined, and a fatty alkyl ester phase separates from the solid amino acid salt, reaction of such a mixture will usually provide a relatively low conversion of the fatty alkyl ester to the desired N-acyl amino acid salt. This provides a helpful tool for predicting the outcome of the acylation reaction.

Not every combination of fatty alkyl ester, amino acid salt, and 10% molar excess of alkoxide catalyst provides a single-phase mixture. We found that while glycinate salts are relatively forgiving in providing a single-phase mixture, other amino acid salts are less forgiving (see results in Table 3, below). Although we do not wish to be bound by any particular theory, it appears that integration of the reactants into a single phase is valuable for achieving high conversions when the amino acid salts are reacted with fatty alkyl esters to give the corresponding N-acyl amino acid salts.

In some aspects, a single-phase mixture may comprise the amino acid salt, the fatty alkyl ester, and at least 10 mole %, based on the amount of fatty alkyl ester, of an alkoxide catalyst. The examples in Table 1 below meet this description.

In another aspect, the single-phase mixture comprises an amino acid salt mixture; this salt mixture comprises a non-glycinate amino acid salt and at least 20 mole %, preferably at least 30 mole %, of a glycinate salt. As the results in Table 3 (col. 3) below illustrate, including 30 mole % of sodium glycinate (based on the total amount of amino acid salts) in addition to the listed amino acid salt and alkoxide base provides a dramatic increase in conversion to the desired N-acyl amino acid salt. The improvement in conversion may be due to the ability of the starting materials to form a single phase in the presence of this proportion of the glycinate.

In another aspect, the single-phase mixture comprises at least a 30 mole % excess, preferably at least a 40 mole % excess, and most preferably at least a 50 mole % excess, of the fatty alkyl ester. Alternatively, the single-phase mixture comprises at least a 30 mole % excess, preferably at least a 40 mole % excess, and most preferably at least a 50 mole % excess, of the amino acid salt. As shown in Table 3 (cols. 4 and 5), for many amino acids, an excess of either the fatty alkyl ester or the amino acid salt appears to work better in achieving high conversions to the N-acyl amino acid salts than using a 1:1 mole ratio of fatty alkyl ester to amino acid salt. Again, this unexpected improvement in conversion may be due to the ability of the starting materials to more easily form a single-phase mixture when an excess of one reactant is used.

The following examples merely illustrate the invention. Those skilled in the art will recognize many variations that are within the spirit of the invention and scope of the claims.

Preparation of an N-Acyl Glycinates

Sample Procedure

A 200-mL stainless-steel Parr reactor is charged with methyl laurate (70.0 g, 0.315 mol), sodium glycinate (31.0 g, 0.317 mol), sodium methoxide (30 wt. % solution in methanol, 10.8 g, 0.060 mol, 19 mole % based on the amount of methyl laurate), and added methanol (50 g, 33 wt. % based on the amount of charged starting materials). The reactor is sealed, heated to 130° C. (at 50 psig), and stirred at 200 rpm for 5 h. The reaction mixture is cooled to room temperature and the pressure is released slowly. The resulting powder is transferred to a crystallization dish and dried overnight to remove residual methanol. Water is added to provide an aqueous mixture of the N-lauryl glycinate salt of desired concentration.

The procedure described here is generally followed using the reactants and conditions outlined in Table 1 to make N-lauryl glycinate and other N-acyl amino acid salts. The percent conversion of fatty methyl ester, yield of N-acyl amino acid salt, and content of by-products (N-acyl dipeptides and fatty acid soap) are determined by $^1$H NMR. The molten product is cooled to room temperature and diluted with water to give an aqueous solution. APHA color is measured using a 20 wt. % aqueous solution of the N-acyl amino acid salt (ASTM D1209).

Methanol is an excellent solvent for preparing N-acyl amino acid salts. For some personal care applications, it may be desirable to remove methanol or avoid it completely. Some options for producing "methanol-free" N-lauryl glycinates:

1. Ethanol or IPA as the solvent. Perform the reaction in ethanol or isopropanol, then strip excess solvent from the aqueous N-lauryl glycinate mixture (about 1 h at 100° C., atmospheric pressure). This method requires as little as 1.8:1 (w:w) water to sodium lauryl glycinate to remove the solvent.

2. Ethanol or IPA as an azeotroping agent. Perform the reaction in methanol, but add a roughly equimolar amount of ethanol or isopropanol as an azeotroping solvent (about 2 h at 100° C., atmospheric pressure). This method uses about 2.5:1 (w:w) water to sodium lauryl glycinate to remove the solvents.

3. Water stripping. Perform the reaction in methanol and use only water to strip the methanol (about 2 h at 100° C., atmospheric pressure). This method uses about 7:1 (w:w) water to sodium lauryl glycinate to remove the methanol.

Preparation of N-Acyl Amino Acid Salts

Isolation of N-Acyl Glycinate Powder

A 200-mL stainless-steel Parr reactor is charged with methyl laurate (70.0 g, 0.315 mol), sodium glycinate (31.0 g, 0.317 mol), sodium methoxide (30 wt. % solution in methanol, 10.8 g, 0.060 mol, 19 mole % based on the amount of methyl laurate), and added methanol (50 g, 33 wt. % based on the amount of charged starting materials). The reactor is sealed, heated to 130° C. (at 50 psig), and stirred at 200 rpm for 5 h. The reaction mixture is cooled to room temperature and the pressure is released slowly.

Methanol is added to the wet powder to form a slurry. The slurry is then filtered through a coarse-frit glass funnel and washed with methanol to collect the N-acyl glycinate salt as a powder. After drying in an oven (60° C.) overnight, the powder is essentially free of methanol and any residual starting materials. The filtrate is concentrated, analyzed to determine the proportions of methyl laurate and/or sodium glycinate, and is reused to make additional N-acyl glycinate salt.

TABLE 1

Inventive Examples: Preparation of N-Acyl Amino Acid Salts

| Ex | NaOMe (mol %) | ROH* (wt. %) | Glycerin (wt. %) | Pres (psig) | Temp (° C.) | Time (h) | Conv. (mol. %) | AAAS yield (mol. %) | FA soap (mol. %) | N-acyl dipeptides (mol. %) | APHA color | notes |
|---|---|---|---|---|---|---|---|---|---|---|---|---|
| 1 | 19 | 33 | 0 | 50 | 130 | 5 | 92 | 70 | 17 | 2.3 | 371 | |
| 2 | 15 | 25 | 12 | 50 | 116 | 6 | 95 | 67 | 23 | 3.7 | 74 | |
| 3 | 15 | 23 | 5.6 | 50 | 115 | 4 | 94 | 74 | 15 | 1.4 | 33 | |
| 4 | 12 | 23 | 5.6 | 50 | 115 | 4 | 90 | 75 | 13 | 1.5 | 70 | heel from #3 used |
| 5 | 19 | 23 | 10 | 35 | 110 | 4 | 99 | 81 | 14 | 1.7 | 25 | |
| 6 | 15 | 32 | 0 | 25 | 105 | 6 | 100 | 89 | 9 | 0 | 26 | BuOH as solvent |
| 7 | 14 | 30 | 3.4 | 45 | 115 | 4 | 88 | 70 | 14 | 1.2 | 78 | 2X scale-up |
| 8 | 22 | 39 | 0 | 17 | 87 | 7 | 98 | 82 | 13 | 0 | 35 | high cat., low T and P |
| 9 | 20 | 39 | 0 | 9 | 75 | 4 | 62 | 56 | 3.6 | 0 | — | incomplete conversion |
| 10 | 30 | 39 | 0 | 68 | 123 | 4 | 75 | 63 | 7.1 | 0 | — | alanine as reactant |
| 11 | 22 | 32 | 0 | 58 | 112 | 4 | 56 | 47 | 6.5 | 0 | — | glutamine as reactant |
| 12 | 22 | 39 | 0 | 7 | 66 | 6 | 88 | 78 | 7 | 0 | 21 | low pressure run |
| 13 | 22 | 42 | 0 | 12 | 92 | 16 | 92 | 82 | 7.7 | 0.7 | 42 | EtOH as solvent |
| 14 | 20 | 40 | 0 | 6 | 75 | 16 | 85 | 33 | 16 | 0 | — | IPA as solvent |
| 15 | 20 | 40 | 0 | 40 | 120 | 3 | 99 | 83 | 12 | 0 | 74 | IPA as solvent |
| 16 | 18 | 35 | 0 | 20 | 90 | 4 | 97 | 93 | 3.5 | 0 | 10 | |
| 17 | 20 | 35 | 0 | 20 | 90 | 3 | 99 | 94 | 5 | 0 | — | |
| 18 | 15 | 40 | 0 | 15 | 85 | 4 | 96 | 93 | 3 | 0 | — | |

*ROH is methanol and amino acid is glycine unless indicated otherwise in notes; the amount of alcohol is wt. % based on the amount of charged starting materials. Amount of NaOMe is the mole % based on the amount of fatty methyl ester charged. Conversion is mole % based on fatty methyl ester. "AAAS yield" is the mole % yield of N-acyl amino acid salt. FA soap (mole %) is the amount of fatty acid salt (soap). APHA color (ASTM D1209) measured at 20% concentration using a 40-mm cell.

TABLE 2

Comparative Examples: Preparation of N-Acyl Amino Acid Salts

| Ex | NaOMe (mol. %) | ROH* (wt. %) | Glycerin (wt. %) | Pres (psig) | Temp (° C.) | Time (h) | Conv. (mol. %) | AAAS yield (mol. %) | FA soap (mol. %) | N-acyl dipeptides (mol. %) | APHA color | notes |
|---|---|---|---|---|---|---|---|---|---|---|---|---|
| C19 | 3.5 | 28 | 0 | 41 | 110 | 2 | 7 | 3.5 | 3 | — | — | |
| C20 | 4.4 | 30 | 0 | 50 | 115 | 7 | 50 | 32 | 8 | — | — | |
| C21 | 4.7 | 25 | 9.3 | 62 | 125 | 8 | 57 | 28 | 18 | — | — | |
| C22 | 6 | 33 | 0 | 50 | 115 | 24 | 54 | 30 | 17 | 4.5 | — | |
| C23 | 6 | 33 | 0 | 95 | 135 | 5 | 46 | 29 | 15 | 2.6 | — | |

TABLE 2-continued

Comparative Examples: Preparation of N-Acyl Amino Acid Salts

| Ex | NaOMe (mol. %) | ROH* (wt. %) | Glycerin (wt. %) | Pres (psig) | Temp (° C.) | Time (h) | Conv. (mol. %) | AAAS yield (mol. %) | FA soap (mol. %) | N-acyl dipeptides (mol. %) | APHA color | notes |
|---|---|---|---|---|---|---|---|---|---|---|---|---|
| C24 | 9.5 | 40 | 7.4 | 72 | 125 | 16 | 92 | 52 | 33 | 7.5 | — | |
| C25 | 9.7 | 26 | 9.5 | 50 | 125 | 6.5 | 50 | 27 | 17 | 1.6 | — | |
| C26 | 7 CaO | 0 | 31 | 0 | 125 | 5 | 100 | 61 | 23 | 6.6 | >500 | CaO |
| C27 | 22 CaO | 39 | 0 | 30 | 100 | 16 | 58 | 27 | 29 | 0.6 | — | more CaO, pressure |
| C28 | 22 | 39 | 0 | 0 | 65 | 2 | 0 | 0 | 23 | 0 | — | reflux in MeOH |
| C29 | 22 | 39 | 0 | 0 | 65 | 16 | 4 | 0 | 40 | 0 | — | reflux in MeOH |
| C30 | 22 | 39 | 0 | 0 | 75 | 6 | 29 | 0 | 20 | 0 | — | reflux in IPA/MeOH |
| C31 | 20 K$_2$CO$_3$ | 42 | 0 | 30 | 115 | 6 | 8 | 0 | 0 | 0 | — | K$_2$CO$_3$/EtOH |
| C32 | 20 NaOH | 40 | 0 | 35 | 115 | 3.5 | 41 | 0 | 36 | 0 | — | NaOH |

*ROH is methanol and amino acid is glycine unless indicated otherwise in notes; the amount of alcohol is wt. % based on the amount of charged starting materials. Amount of NaOMe or other base is the mole % based on the amount of fatty methyl ester charged. Conversion is mole % based on fatty methyl ester. "AAAS yield" is the mole % yield of N-acyl amino acid salt. FA soap (mole %) is the amount of fatty acid salt (soap). APHA color (ASTM D1209) measured at 20% concentration using a 40-mm cell.

Effect of Single-Phase Mixture

The procedure described above for making N-acyl glycinates is generally used with Steposol® C-42 (methyl laurate/methyl myristate mixture) and salts of the amino acids identified in Table 3.

As shown in column 2 of Table 3, the reaction is somewhat hit or miss when glycine is not used. When serine and alanine salts are combined with Steposol® C-42 and the alkoxide base, a single-phase mixture of the starting materials is generated, and reaction of this mixture provides good conversions (67-87%) to the N-acyl amino acid salts. In contrast, other amino acid salts form a two-phase mixture of starting materials with Steposol® C-42 and the alkoxide base, and reaction of the two-phase mixture gives 50% or less of the desired product.

In another series of experiments, the procedure is modified by including 30 mole % of sodium glycinate (based on the total amount of amino acid salts) in addition to the listed amino acid salt and alkoxide base (Table 3, column 3). As shown in the table, conversions increase dramatically in the presence of added sodium glycinate, which coincidentally helps to generate a single-phase mixture of the reactants.

In other experiments, the procedure is modified again, not by including any glycinate, but by altering the proportions of Steposol® C-42 and the amino acid salt. In one series (Table 3, column 4), a 1.5:1 molar excess of the methyl ester is used. In another series (Table 3, column 5), a 1.5:1 molar excess of the amino acid salt is used. Interestingly, an excess of either reactant outperforms a 1:1 molar ratio. The remarkable improvement in conversion may be due at least in part to the ability to achieve a single-phase mixture of the starting materials when an excess of either reactant is used.

TABLE 3

Preparation of N-Acyl Amino Acid Salts: Effect of Single-Phase Mixture

| | Conversion to N-Acyl Amino Acid Salt, % | | | |
|---|---|---|---|---|
| Amino acid | 1:1 molar ME:AA | 30 mol % Na glycinate included | 1.5:1 molar ME:AA | 1.5:1 molar AA:ME |
| valine | 50* | 95 | — | 85 |
| histidine | 47* | — | 80 | — |
| proline | 39* | 80 | — | 90 |
| serine | 87 | — | — | — |
| glutamine | 48* | 90 | 75 | — |
| aspartic acid | 21* | — | — | 94 |
| lysine | 45* | 86 | — | — |
| alanine | 67 | — | — | — |
| sarcosine | 22* | 96 | 90 | — |

ME = Steposol ® C-42 (product of Stepan).
AA = amino acid salt
*reactants form a two-phase mixture (comparative examples)

The preceding examples are meant only as illustrations. The following claims define the invention.

We claim:

1. A process which comprises reacting a fatty alkyl ester with an amino acid salt in the presence of at least 10 mole %, based on the amount of fatty alkyl ester, of an alkoxide catalyst at a pressure of at least 5 psig to produce a composition comprising an N-acyl amino acid salt.

2. The process of claim 1 wherein the catalyst comprises a C$_1$-C$_4$ alkoxide.

3. The process of claim 1 wherein the catalyst is sodium methoxide/methanol.

4. The process of claim 1 wherein the catalyst is used in an amount within the range of 12 to 50 mole %.

5. The process of claim 1 wherein the reaction is performed at a pressure within the range of 5 psig to 50 psig.

6. The process of claim 1 wherein the fatty alkyl ester is a C$_6$-C$_{22}$ methyl ester.

7. The process of claim 1 wherein the amino acid salt is an alkali metal salt of an amino acid selected from the group consisting of glycine, alanine, glutamine, glutamic acid, and aspartic acid.

8. The process of claim 1 wherein the amino acid salt is an alkali metal salt of glycine.

9. The process of claim 1 wherein the reaction is performed in the presence of a polyol selected from the group consisting of glycerin and propylene glycol.

10. The process of claim 1 wherein the reaction is performed at a temperature within the range of 65° C. to 200° C.

11. The process of claim 1 wherein the reaction is performed in the presence of 1 to 200 wt. %, based on the amount of fatty alkyl ester, of an added alcohol solvent.

12. The process of claim 11 wherein the reaction is performed in the presence of 40 to 80 wt. % of the alcohol solvent.

13. The process of claim 1 wherein the N-acyl amino acid salt is isolated from unreacted starting materials in the N-acyl amino acid salt composition by forming a slurry of the composition in a $C_1$-$C_4$ alcohol, recovering the N-acyl amino acid salt from the slurry, and drying the N-acyl amino acid salt.

14. The process of claim 1 wherein the amino acid salt is a mixture comprising a glycinate salt and a non-glycinate amino acid salt, wherein the salt mixture comprises at least 20 mole % of the glycinate salt.

15. A process which comprises reacting a $C_6$-$C_{22}$ methyl ester with a glycinate salt in the presence of at least 10 mole %, based on the amount of $C_6$-$C_{22}$ methyl ester, of an alkoxide catalyst at a pressure within the range of 5 psig to 30 psig and a temperature within the range of 65° C. to 100° C. to produce an N-acyl glycinate salt composition.

* * * * *